US007027865B2

United States Patent
Erickson et al.

(10) Patent No.: US 7,027,865 B2
(45) Date of Patent: Apr. 11, 2006

(54) PACEMAKER WITH VASOVAGAL SYNCOPE DETECTION AND THERAPY

(75) Inventors: Mark K. Erickson, Brooklyn Park, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 530 days.

(21) Appl. No.: 10/414,908

(22) Filed: Apr. 16, 2003

(65) Prior Publication Data

US 2004/0210260 A1    Oct. 21, 2004

(51) Int. Cl.
*A61N 1/36* (2006.01)
(52) U.S. Cl. ............................................. 607/9; 607/25
(58) Field of Classification Search .................... 607/9, 607/14, 25
See application file for complete search history.

(56) References Cited

U.S. PATENT DOCUMENTS

| 4,556,063 A | 12/1985 | Thompson et al. | |
|---|---|---|---|
| 5,127,404 A | 7/1992 | Wyborney et al. | |
| 5,284,491 A | 2/1994 | Sutton et al. | |
| 5,441,525 A | 8/1995 | Shelton et al. | |
| 5,501,701 A | 3/1996 | Markowitz et al. | |
| 5,540,728 A | 7/1996 | Shelton et al. | |
| 5,676,686 A | 10/1997 | Jensen et al. | |
| 6,889,078 B1* | 5/2005 | Struble et al. | 607/9 |
| 2002/0004670 A1 | 1/2002 | Florio et al. | 607/9 |

FOREIGN PATENT DOCUMENTS

WO    WO 95/29734    11/1995

* cited by examiner

*Primary Examiner*—Robert E. Pezzuto
*Assistant Examiner*—Tammie Heller
(74) *Attorney, Agent, or Firm*—Paul H. McDowall; Girma Walde-Michael

(57) ABSTRACT

A method and apparatus for cardiac pacing are provided in which pacing pulses are delivered at an increased rate in response to a detected intrinsic heart rate drop and a special rate drop response detection scheme is temporarily disabled until an intrinsic heart rate exceeds a predetermined threshold value. If the pacing rate reaches the lower pacing rate without sensing intrinsic activity, heart rate drop detection remains disabled and lower rate pacing continues. Rate drop detection is re-enabled whenever sufficient sensed intrinsic activity indicates that a sudden intrinsic rate drop could occur again. Thus, the subsequent reduction in heart rate requiring therapy is declared only if a sensed intrinsic heart rate drops from above an intermediate value (herein defined as a re-enable rate) that is set above the lower pacing rate and an upper pacing rate.

10 Claims, 5 Drawing Sheets

PACEMAKER WITH VASOVAGAL SYNCOPE DETECTION AND THERAPY

FIELD OF THE INVENTION

The present invention relates generally to cardiac pacing devices and more specifically to a cardiac pacemaker device for providing an electrical stimulation therapy upon detection of vasovagal syncope or other vasodepressor or cardioinhibitory disorders.

BACKGROUND OF THE INVENTION

Vasovagal syncope is a condition marked by a sudden drop in heart rate and blood pressure, resulting in fainting. It is not only unpleasant for a patient, but potentially dangerous, as fainting may lead to injuries from falls. U.S. Pat. No. 5,284,491, issued to Sutton et al. (the '491 patent) discloses a cardiac pacemaker specifically adapted to treat patients suffering from vasovagal syncope. In particular, according to the '491 patent the pacemaker detects when the patient's heart rate drops below a lower "hysteresis" rate and determines whether the average rate of decrease in the patient's heart rate, over a defined number of heartbeats or a defined time interval prior to reaching the "hysteresis" rate, is greater than a preset value. If so, the pacemaker's rate is set equal to the "hysteresis" rate and thereafter increased to an "intermediate" rate substantially higher than the "hysteresis" rate. The pacemaker's rate remains at the "intermediate" rate for a preset time period and thereafter gradually declines to a lower pacing rate.

Various improvements have been proposed for detecting a heart rate drop and responding to a rate drop with interventional pacing. In U.S. Pat. No. 5,441,525, issued to Shelton, et al., incorporated herein by reference in its entirety, a stability and intervention procedure is proposed in which transient drops in rate are ignored and pacing at a predetermined high rate occurs if the drops are stable. A sleep disable feature disables the vasovagal syncope detection and therapy features during the patient's sleeping hours to reduce or eliminate false positive responses. In U.S. Pat. No. 5,501,701, issued to Markowitz et al., incorporated herein by reference in its entirety, a method is disclosed in which pacing pulses are provided at an increased rate in response to a rapid drop detected when the heart rate falls from a persistent rate above a first threshold rate to a stable rate below a second threshold rate. If spontaneous depolarizations are detected while pacing at the increased rate, pacing at the increased rate is terminated.

In U.S. Pat. No. 5,676,686 issued to Jensen, et al., incorporated herein by reference in its entirety, a rapid drop in heart rate may be detected in response to a drop of greater than a defined amount from the highest detected heart rate over a preceding time period. Alternatively, an unbroken sequence of pacing pulses delivered at a base pacing rate may trigger pacing at an increased pacing rate. The latter rate drop detection criterion is advantageous in patients that experience unpredictable rate drop episodes. As implemented in the commercially available Medtronic Kappa™ 700 pacemaker, a rate drop response provides pacing at an elevated rate for a brief period of time following a drop in heart rate which meets programmed rate drop detection criteria. To detect rate drop episodes in patients having episodes that are predictable in drop size and suddenness, a drop rate, drop size and detection window can be programmed to provide relatively specific rate drop detection. In patients that experience unpredictable rate drop episodes, more general rate drop detection criteria based on lower rate pacing for a predetermined number of consecutive detection beats may be programmed. In patients having both predictable and unpredictable rate drop episodes, both the lower rate criterion and the rate drop size and suddenness criteria and can be enabled to detect a rate drop.

Generally, a rate drop response delivers higher rate pacing for a predetermined interval of time after which the pacing rate is gradually reduced back to the programmed lower rate. If rate drop detection criteria includes a the lower rate criterion and no intervening intrinsic cardiac activity is sensed as the pacing rate is reduced from a high rate back to the lower rate, the rate drop response will be re-triggered after pacing returns to the lower rate even though an intrinsic rate drop has not actually occurred. If the intrinsic heart rate remains below the programmed lower rate, a cyclical pattern of false rate drop detections and pacing intervention will continue. This cyclical pattern will be disrupted only when intrinsic heart activity is sensed above the lower rate, thereby inhibiting pacing output and preventing another detection of a rate drop according to the lower rate criterion. If the patient's intrinsic rate is lower than the programmed lower rate, for example while sleeping, repetitive re-triggering of the rate drop response can occur. Such repetitive intervention is unneeded and undesirable since pacemaker battery energy is unnecessarily consumed and the patient's sleep may be disrupted. For patients that do not experience rate drop episodes at night, a sleep disable feature can prevent false rate drop detections at night as disclosed in the above cited '525 patent to Shelton. However, in some patients, the lower rate criterion may be needed to ensure that unpredictable rate drop episodes are detected night or day.

A need remains, therefore, for providing a cardiac pacing device and method for detecting and treating a heart rate drop, associated with vasovagal syncope, or other vasodepressive or cardioinhibitory disorders such as carotid sinus syndrome, that avoids repetitive rate drop response interventions triggered by a lower rate criterion enabled to detect unpredictable rate drop episodes.

SUMMARY OF THE INVENTION

The present invention provides an improved cardiac pacing device and method for providing therapy in treating patients with vasovagal syncope. Specifically, the method prevents false rate drop detection based on lower rate criterion and repetitive re-triggering of rate drop response pacing during sustained periods of low intrinsic heart rate.

According to the present invention, when an intrinsic (or physiologic) heart rate drops such that the drop, or reduction, in the heart rate satisfies certain rate drop detection criteria, a predetermined pacing therapy is provided. Following detection of such a heart rate drop, the rate drop detection criteria is adjusted so that only a subsequent, physiologic rate drop triggers the pacing therapy. This contrasts with prior art rate drop response algorithms wherein if a patient's intrinsic heart rate is lower than a lower rate (LR) the elevated pacing therapy provided in response to detection of a rate drop repetitively triggers when the such elevated rate is reduced to the LR. According to the present invention, a rate drop detection scheme is temporarily suspended subsequent to an initial heart rate drop that precipitated a curative cardiac pacing therapy. Thus, the subsequent heart rate drop requiring therapy is declared only if a sensed intrinsic heart rate drops from above an intermediate value (herein defined as a re-enable rate (RR)) set above a LR and an upper rate. Herein the upper rate is call the intervention rate (IR).

An initial rate drop is declared if a predetermined threshold number of consecutively paced beats are delivered at the LR (also referred to as the base rate) following a relatively higher intrinsic heart rate (due to normal sinus rhythm or NSR). Upon detection of an initial rate drop, the rate drop detection feature is temporarily disabled, and a rate drop pacing therapy response is provided. The rate drop response typically comprises by a relatively elevated pacing rate for a predetermined period of time followed by a gradual reduction in the pacing rate (e.g., a series of step changes in the pacing rate). The pacing rate gradually returns to the lower rate. If the lower rate is reached without sensing intrinsic cardiac activity, lower rate pacing continues.

Temporarily disabling the rate drop detection feature prevents a re-triggering of rate drop response pacing due to LR pacing during a sustained, low intrinsic heart rate. That is, if the NSR of a patient is less than the programmed LR, certain prior art rate drop response schemes may oscillate between the LR and the IR. According to the present invention rate drop detection is re-enabled upon satisfaction of certain re-enabling criteria. The re-enabling criteria requires enough intrinsic activity to be sensed such that a subsequent rate drop is physiologically possible. In one embodiment, the re-enabling criteria includes detection of a predetermined number of sensed cardiac events at or greater than a predetermined rate above the programmed lower rate (i.e., the RR).

DETAILED DESCRIPTION OF THE INVENTION

Figure 1:
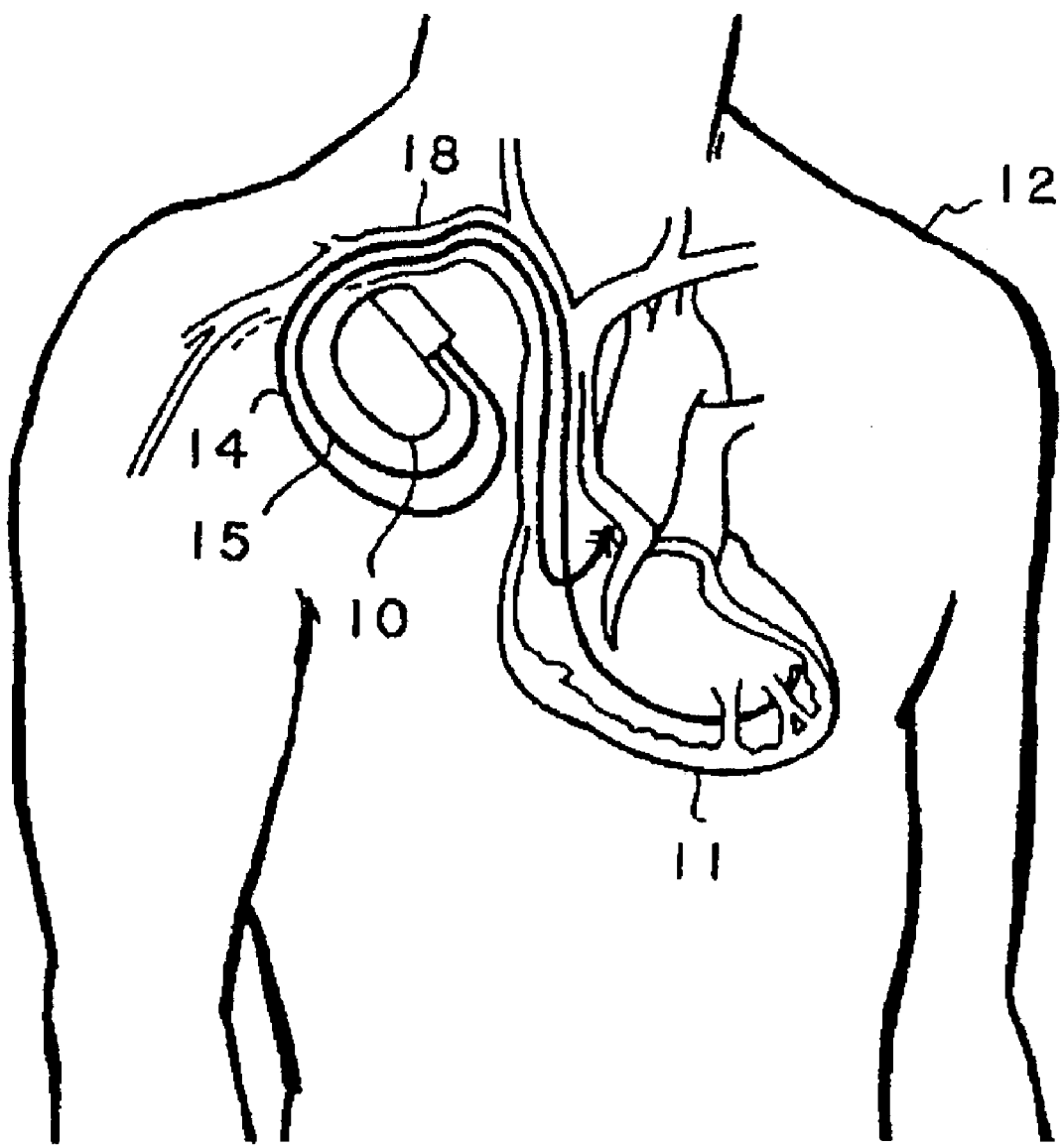
FIG. 1 is a diagram showing the heart of a patient electrically connected to a pacemaker of a type suitable for practicing the present invention.

FIG. 1 generally shows a pacemaker 10, of a type suitable for practicing the present invention, implanted in a patient 12. The pacemaker illustrated is a dual chamber, rate responsive pacemaker, capable of sensing demand for cardiac output and of pacing the atrium and ventricle, but the invention may also be practiced in conjunction with non-rate responsive pacemakers and pacemakers which pace and/or sense in only one chamber of the heart or in three or all four heart chambers. The pacemaker is provided with leads 14, 15, which electrically couple the pacemaker 10 to the ventricle and atrium, respectively, of the patient's heart 11 via electrodes located thereon. The electrodes are employed to sense depolarizations of the heart, referred to informally herein as "beats" and to deliver pacing pulses to the heart.

Figure 2:
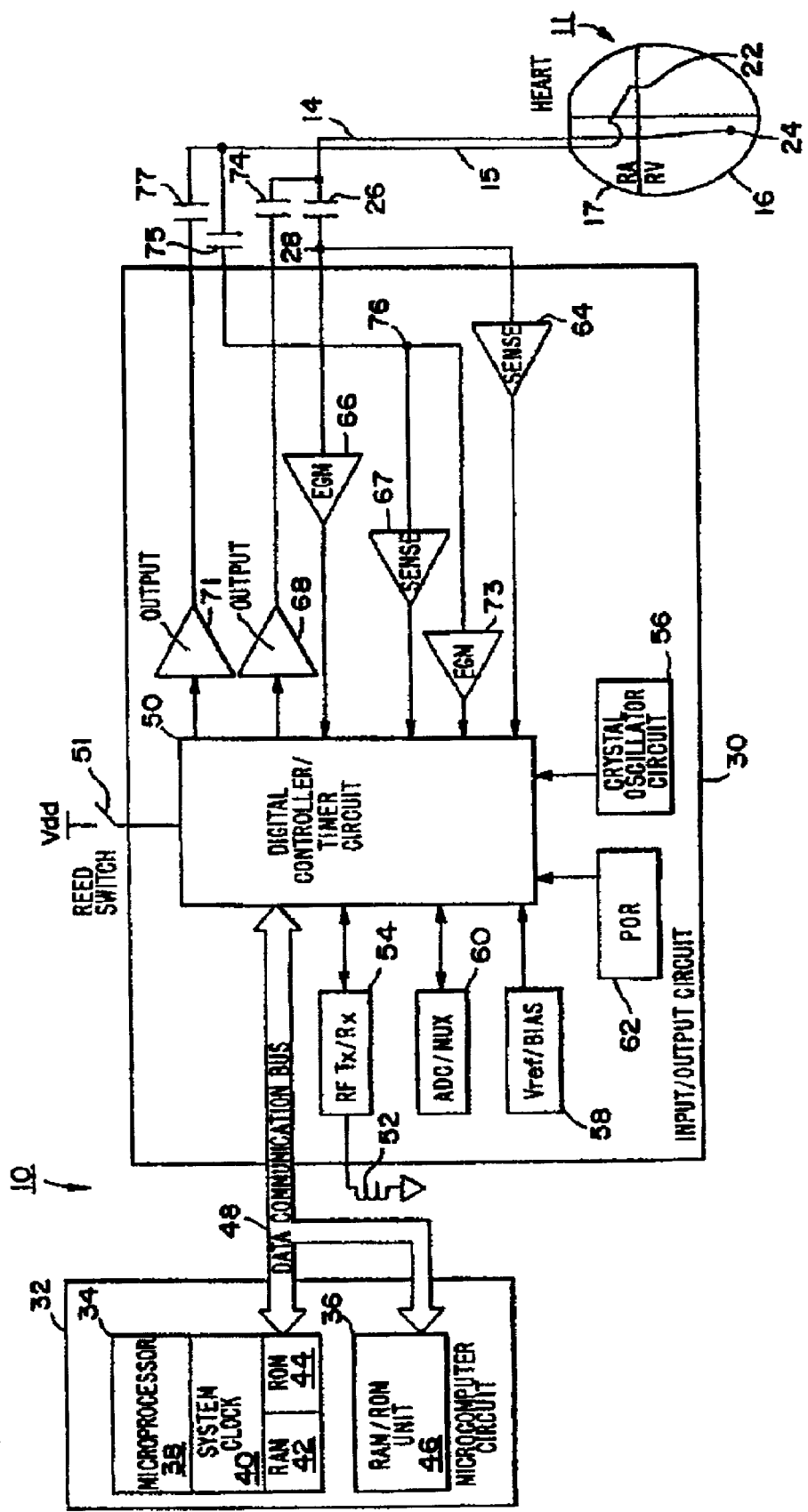
FIG. 2 is a schematic block diagram of the implantable pacemaker shown in FIG. 1.

FIG. 2 is a block circuit diagram illustrating a multi-programmable, implantable, dual-chamber, bradycardia pacemaker 10 capable of carrying out the present invention. Although the present invention is described in conjunction with a microprocessor-based architecture, it will be understood that it could be implemented in other technology such as digital logic-based, custom integrated circuit (IC) architecture, if desired. It will also be understood that the present invention may be implemented in cardiac pacing devices which include cardioversion and defibrillator capabilities and the like.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14, 15 as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 51 is connected to Input/Output Circuit 30 to enable patient follow-up via disabling the sense amplifier(s) and enabling telemetry and programming functions, as is known in the art.

A Crystal Oscillator Circuit 56, typically a 32,768 Hz crystal-controlled oscillator, provides main timing clock signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-service (EOS) function. A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64,67 to electrogram (EGM) amplifiers 66,73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64,67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention, and which is incorporated herein by reference.

Figure 3:
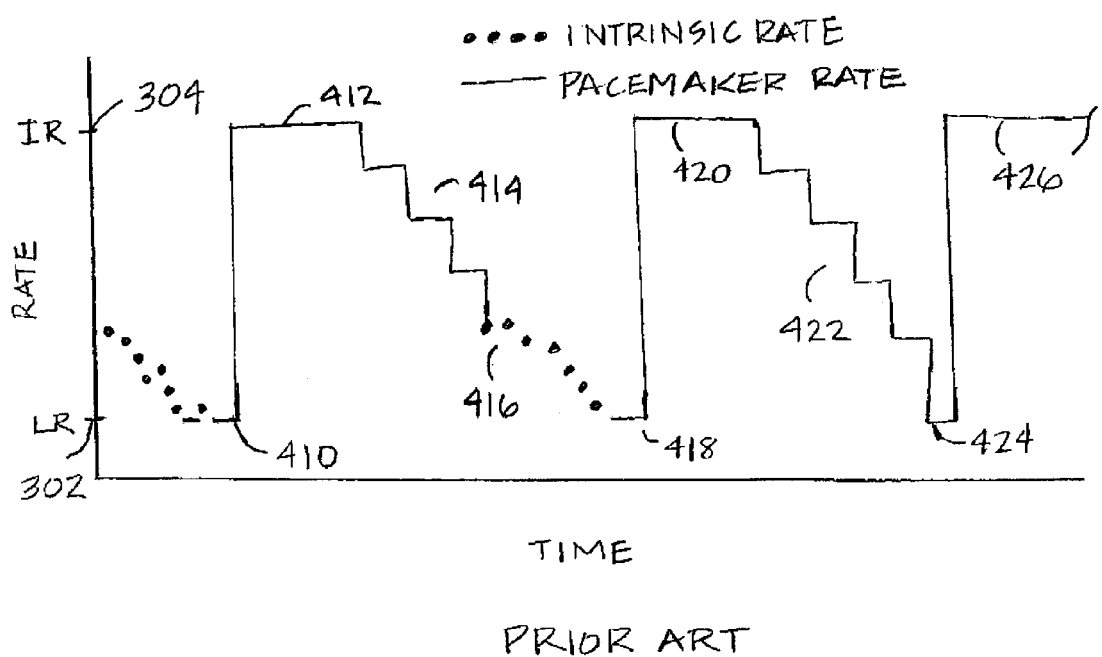
FIG. 3 is a graph of heart rate and pacemaker rate versus time illustrating a rate drop detection mode of operation based on a lower rate criterion and a therapy feature according to prior art.

Output pulse generators 68,71 provide the pacing stimuli to the patient's heart 11 through output capacitors 74,77 and leads 14,15 in response to paced trigger signals developed by Digital Controller/Timer Circuit 50 each time the escape interval times out, or an externally transmitted pacing command has been received, or in response to other stored commands as is well known in the pacing art. In a preferred embodiment of the present invention, pacemaker 10 is capable of operating in various non-rate-responsive odes which include DDD, DDI, VVI, AII, ADI, VOO and VVT, as well as corresponding rate-responsive modes of same. FIG. 3 illustrates details of a rate drop detection mode and therapy feature according to prior art in which a rate drop is detected based on a lower rate criterion. A lower rate (LR) 302 is shown—a lower threshold for a paced heart rate (also known as the base escape rate or the base pacing rate of the pacemaker). This rate may be, for example, 50–70 beats per minute. An intervention rate (IR) 304 is the rate that the pacemaker will begin to provide cardiac pacing stimulation in response to rate drop detection. This rate is substantially above the lower rate. The values of the LR and IR are programmable (by a physician or other clinician) and, of course, the IR should be equal to or less than the maximum pacing rate attainable by the pacemaker, in the case of rate-responsive or dual chamber (e.g. DDD or VDD) pacemakers.

The intrinsic heart rate is illustrated by dotted line, determined beat-by beat based on the time interval separating the current beat from the previous beat. The escape rate of a pacemaker is illustrated by the solid line segments. If the invention is practiced in a single chamber pacemaker (e.g., VVI or AAI) the pacemaker will be inhibited from delivering pacing pulses when the patient's heart rate is higher than the pacemaker's escape rate. If the pacemaker is an atrial synchronized, dual chamber pacemaker (e.g. DDD or VDD pacing mode), the pacemaker will pace synchronized to the patient's intrinsic rate when the patient's rate is higher than the pacemaker's escape rate. In dual chamber modes, which are synchronized to the atrium, it is contemplated that the atrial heart rate will generally be monitored. For simplicity, it is assumed that the pacemaker is not set to a rate responsive mode, and that therefore the pacemaker's escape rate is initially equal to a fixed LR 302.

The pacemaker stores the intervals associated with successive heart beats, keeping a record of the preceding series of beats. A rate drop is detected upon a predetermined, usually programmable, number of paced beats at the lower rate, for example, 1, 2 or 3 paced beats at the lower rate. In the example shown, a rate drop is detected at 410 upon the required number of consecutively paced beats at the LR. A therapeutic intervention is provided by increasing the pacemaker's escape rate to the IR 304, at 412. In the absence of faster spontaneous, or NSR, heart rates, the escape rate remains at the intervention rate for a programmed period of time and thereafter gradually declines at 414 until intrinsic activity greater than the LR 302 is sensed at 416 or, if no intrinsic activity is sensed, until the LR 302 is reached. If the patient's spontaneous rate exceeds the IR, the escape rate of the pacemaker resets to the LR, and aborts the therapeutic rate drop intervention. A more detailed description of the therapeutic intervention illustrated is set forth in the above-cited Shelton patent, U.S. Pat. No. 5,540,728.

In the example shown in FIG. 3, a second rate drop detection occurs based on the lower rate criterion at 418 followed by interventional pacing at 420. The pacing rate is gradually reduced at 422 back down to the lower rate 302 at 424. Since no intrinsic activity greater than the lower rate 302 is sensed the LR 302 is reached. The required number of consecutively paced beats at the lower rate at 424 satisfies the lower rate criterion for rate drop detection, re-triggering the rate drop response therapy, and the pacemaker rate returns to the IR at 426. Thus, when lower rate criterion for rate drop detection is enabled, retriggering of the rate drop response therapy can occur repeatedly upon false rate drop detections, as illustrated by FIG. 3, if no intrinsic activity is sensed following interventional pacing.

Figure 4:
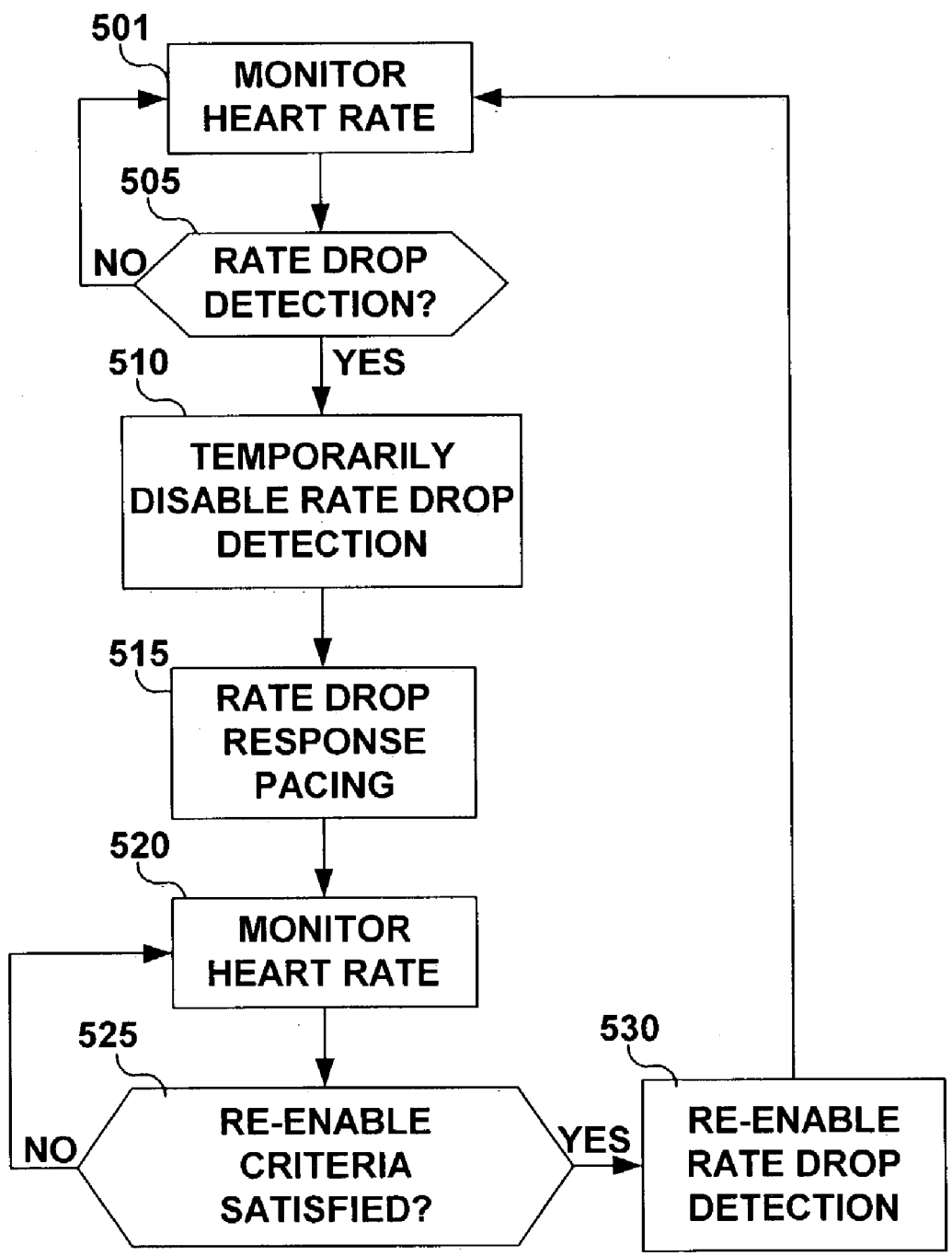
FIG. 4 is a flow chart summarizing steps included in an improved method for detecting and responding to a rate drop episode which may be implemented in the pacemaker shown in FIG. 2 or the like in accordance with the present invention.

FIG. 4 is a flow chart summarizing steps included in an improved method for detecting and responding to rate drop episodes based on lower rate criterion which may be implemented in the pacemaker shown in FIG. 2, or the like, in accordance with the present invention. Method 500 begins at step 501 by monitoring the heart rate for changes that satisfy selected rate drop detection criteria. Selected detection criteria include a lower rate criterion for rate drop detection and may additionally include alternative rate drop detection criteria relating to the suddenness, size and stability of the rate drop as compared to recent cardiac activity of a patient. As defined previously, the lower rate criterion requires a predetermined number of paced beats at the programmed lower rate in order to detect a rate drop episode. Additional rate drop criteria may correspond to the rate drop detection methods generally disclosed in the above-referenced '525, '701, and '686 patents.

At decision step 505, method 500 determines if a rate drop is detected according to programmed detection criteria. If a rate drop is not detected, heart rate monitoring at step 501 continues. When a rate drop is detected at step 505, rate drop detection is temporarily disabled at step 510. Interventional rate drop response pacing is delivered at step 515. The rate drop response pacing may be provided according to known algorithms for treating a vasovagal syncope or other vasodepressor or cardioinhibitory episode. As indicated above in conjunction with FIG. 3, a rate drop response therapy typically includes pacing for a period of time at a relatively high rate, for example on the order of 90 to 110 beats per minute, and then gradually reducing the pacing rate back to the lower rate, for example in five beat per minute (bpm) or equivalently in five pace per minute (ppm) stepwise decrements per minute.

Temporarily disabling rate drop detection at step 510 prevents re-triggering of rate drop response pacing if the lower rate is reached with no intervening intrinsic activity, indicating a sustained, low intrinsic rate is present and not a rate drop. A sudden NSR rate drop such as is often associated with vasovagal syncope by definition can only occur after an NSR heart rate has risen again to some rate greater than the lower rate. Therefore rate drop detection should only occur after sufficient intervening intrinsic, or NSR, cardiac activity above the LR has been sensed. That is, a NSR heart rate above the LR indicates a rate drop can occur.

During and after rate drop response pacing, the heart rate is monitored as indicated at step 520 to determine if rate drop detection re-enabling criteria are satisfied at decision step 525. Rate drop detection is re-enabled when sufficient intrinsic activity has been sensed following a rate drop intervention indicating a true rate drop could occur again. In one embodiment, re-enable criteria require that a predetermined number of consecutively sensed intrinsic heartbeats occur above a re-enabling rate. For example, at least three consecutively sensed intrinsic beats at a rate greater than the programmed lower rate plus five beats per minute may re-enable rate drop detection. Until the re-enable criteria are satisfied, rate drop detection remains temporarily disabled and heart rate monitoring for intrinsic activity above the re-enabling rate continues at step 520.

Once the re-enable criteria are satisfied, rate drop detection is re-enabled at step 530, and method 500 returns to step 501 to wait for the next rate drop detection based on lower rate criterion or any other programmed detection criteria.

Figure 5:
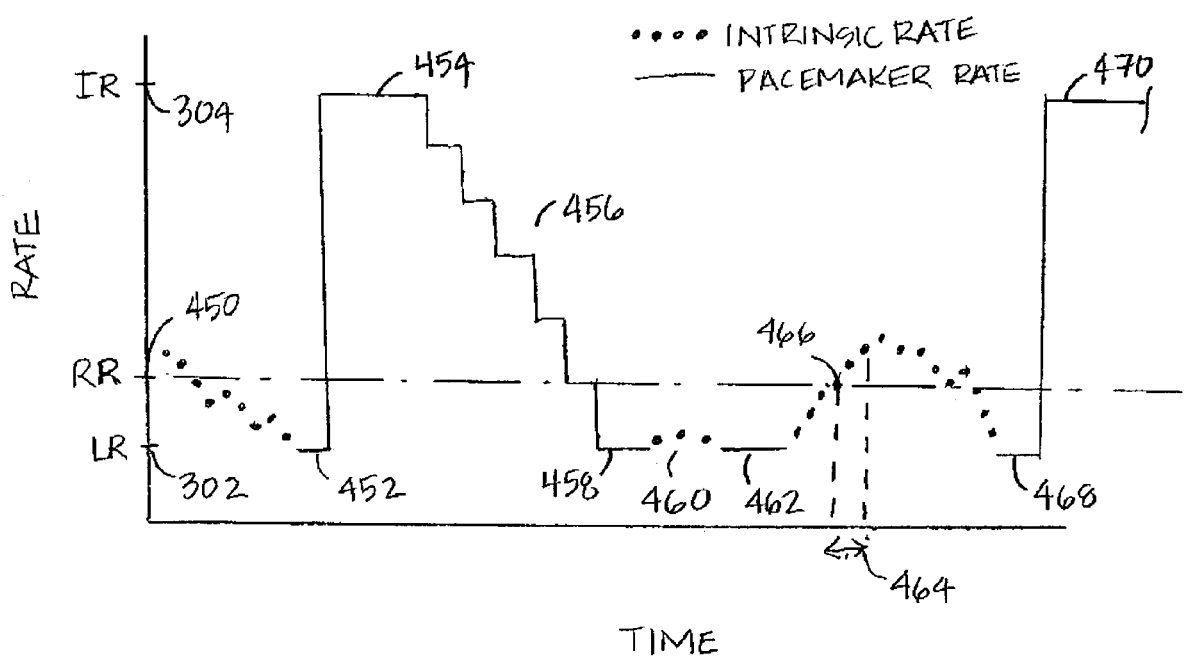
FIG. 5 is a graph of heart rate and pacemaker rate versus time illustrating the operation of the method of FIG. 4.

FIG. 5 illustrates the operation of method 500 of FIG. 4. A selected lower rate (LR) 302 and intervention rate (IR) 304 are indicated and correspond to the LR and IR described previously in conjunction with FIG. 3. A re-enable rate (RR) 450 is selected as a rate above which intrinsic activity must be sensed in order to re-enable rate drop detection after it has been disabled. The RR 450 is generally greater than the lower rate 302 and less than the intervention rate 304, typically five to 10 beats greater than the lower rate. The sensed intrinsic heart rate is indicated by dotted line and the pacing rate is indicated by solid line. A rate drop detection based on a predetermined number of paced beats at the lower rate is made at 452 resulting in rate drop response pacing at the intervention rate 304 at 454 followed by a gradual reduction in pacing rate at 456 back to the lower rate 302 at 458.

No intrinsic cardiac activity is sensed during the reduction of the pacing rate back to the lower rate at 458. According to method 500 described above, rate drop detection is disabled resulting in sustained lower rate pacing. Some intrinsic activity is sensed at 460 disrupting lower rate pacing. However, the intrinsic activity is below the re-enable rate 450. Therefore, rate drop detection remains disabled, and lower rate pacing continues at 462. Intrinsic activity greater than the re-enable rate is detected at 466. After a required number of consecutive intrinsic beats greater than the RR 450, rate drop detection is re-enabled at 464. Subsequently, another drop in the intrinsic rate resulting in lower rate pacing at 468 re-triggers rate drop response pacing at the intervention rate 304 at 470.

Methods according to the present invention may be performed by an any medical device having the ability to sense cardiac activity and provide cardiac pacing stimulus, such as a pacemaker, an cardioverter-defibrillator and the like. The present invention may be practiced with temporary pacing leads, subcutaneous or transcutaneous medical electrical leads. The pacing engine may be programmable and/or part of an external medical device.

Thus, a method has been described for detecting and providing therapy for treating an intrinsic heart rate drop which may be associated with vasovagal syncope or other disorders such as neurogenic syncope, carotid sinus syndrome, or other vasodepressor or cardioinhibitory disorders. The method described herein advantageously prevents repetitive re-triggering of a rate drop therapy when intrinsic cardiac activity supporting the possibility of an intrinsic heart rate drop is not present. Variations and modifications may be made to the detailed embodiments presented herein. The described embodiments should therefore be considered exemplary, not limiting, with regard to the following claims.

What is claimed is:

1. A method of cardiac pacing, comprising:
   detecting a series of intrinsic depolarizations of a heart;
   detecting a reduction in an intrinsic heart rate for at least two of the series of intrinsic depolarizations that satisfy a predetermined rate drop criteria;
   delivering a cardiac pacing therapy at a first pacing rate, above the intrinsic heart rate, in response to the detection of the reduction in the intrinsic heart rate;
   temporarily disabling the detection of the reduction in the intrinsic heart rate;
   delivering a series of cardiac pacing pulses at a second pacing rate that is less than the first pacing rate;
   defining a re-enabling rate; and
   re-enabling the detection of the reduction in the intrinsic heart rate upon detection of a predetermined number of intrinsic heart depolarizations greater than the re-enabling rate.

2. A method according to claim 1, wherein the first pacing rate is at least twenty beats per minute above the intrinsic heart rate.

3. A method according to claim 1, wherein the re-enabling rate is defined as more than five beats per minute above the first pacing rate.

4. A method according to claim 1, wherein the second pacing rate further comprises gradually reducing the second pacing rate to a predetermined lower rate.

5. A method according to claim 1, wherein the second pacing rate further comprises reducing the second pacing rate in a series of step changes in the second pacing rate.

6. A method according to claim 1, further comprising: storing at least one data item related to the step of detecting a reduction in the intrinsic heart rate.

7. A computer readable medium for storing instructions for performing a method, comprising:
   instructions for detecting a series of intrinsic depolarizations of a heart;
   instructions for detecting a reduction in an intrinsic heart rate for at least two of the series of intrinsic depolarizations that satisfy a predetermined rate drop criteria;
   instructions for delivering a cardiac pacing therapy at a first pacing rate, above the intrinsic heart rate, in response to the detection of the reduction in the intrinsic heart rate;

instructions for temporarily disabling the detection of the reduction in the intrinsic heart rate;

instructions for delivering a series of cardiac pacing pulses at a second pacing rate that is less than the first pacing rate;

instructions for defining a re-enabling rate; and instructions for re-enabling the detection of the reduction in the intrinsic heart rate upon detection of a predetermined number of intrinsic heart depolarizations greater than the re-enabling rate.

8. A computer readable medium according to claim 7, further comprising:

Instructions for storing at least one data item related to the step of detecting a reduction in the intrinsic heart rate.

9. A cardiac pacing apparatus, comprising:

means for detecting a series of intrinsic depolarizations of a heart;

means for detecting a reduction in an intrinsic heart rate for at least two of the series of intrinsic depolarizations that satisfy a predetermined rate drop criteria;

means for delivering a cardiac pacing therapy at a first pacing rate, above the intrinsic heart rate, in response to the detection of the reduction in the intrinsic heart rate;

means for temporarily disabling the detection of the reduction in the intrinsic heart rate;

means for delivering a series of cardiac pacing pulses at a second pacing rate that is less than the first pacing rate;

means for defining a re-enabling rate; and means for re-enabling the detection of the reduction in the intrinsic heart rate upon detection of a predetermined number of intrinsic heart depolarizations greater than the re-enabling rate.

10. A cardiac apparatus according to claim 9, further comprising:

means for storing at least one data item related to the step of detecting a reduction in the intrinsic heart rate.

* * * * *